| [19] | [11] Patent Number: | 4,749,718 |
|---|---|---|
| | [45] Date of Patent: | Jun. 7, 1988 |

United States Patent
Coates et al.

[54] CARBAZOLE DERIVATIVES AND THEIR USE AS 5HT-INDUCED ANTAGONISTS

[75] Inventors: Ian H. Coates, Hertford; James A. Bell, Ware; David C. Humber, Ealing; George B. Ewan, Chalfont St. Peter, all of England

[73] Assignee: Glaxo Group Limited, United Kingdom

[21] Appl. No.: 888,257

[22] Filed: Jul. 23, 1986

[30] Foreign Application Priority Data

Jul. 24, 1985 [GB] United Kingdom ................. 8518745

[51] Int. Cl.⁴ ..................... A61K 31/40; C07D 403/06
[52] U.S. Cl. ................................... 514/397; 548/336; 548/439
[58] Field of Search ................. 548/336, 439; 514/397

[56] References Cited

U.S. PATENT DOCUMENTS

| 3,634,420 | 1/1972 | Littell et al. | 548/336 |
| 3,671,544 | 6/1972 | Meltzer et al. | 548/439 |
| 4,334,070 | 6/1982 | Berger et al. | 548/336 |
| 4,740,404 | 6/1982 | Littell et al. | 548/336 |

FOREIGN PATENT DOCUMENTS

| 0115607 | 8/1984 | European Pat. Off. | 548/336 |
| 1108578 | 10/1965 | United Kingdom | 548/336 |
| 1201061 | 8/1967 | United Kingdom | 548/336 |

OTHER PUBLICATIONS

R. Littell, E. N. Greenblatt and G. R. Allen, Jr., J. Med. Chem. 15(8) 875-6, 1972.
Evans, D. D., Aust. J. Chem.; 26(11), 2555-8, 1973.
J. C. Lancelot, et al., Chem. & Pharm. Bul., 1983, 31, 2652-2661.
Y. Oikawa et al., J. Org. Chem., 1977, 42, 1213-1216.

*Primary Examiner*—Alan L. Rotman
*Assistant Examiner*—J. Richter

*Attorney, Agent, or Firm*—Bacon & Thomas

[57] ABSTRACT

The invention relates to compounds of the general formula (I):

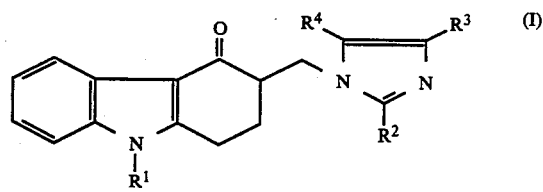

wherein
$R^1$ represents a group $CO_2R^5$, $COR^5$, $CONR^5R^6$ or $SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl-($C_{1-4}$)alkyl group in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $CO_2R^5$ or $SO_2R^5$);
and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group; and physiologically acceptable salts and solvates thereof.

The compounds are potent and selective antagonists of "neuronal" 5-hydroxytryptamine receptors and are useful in the treatment of psychotic disorders (e.g. schizophrenia and mania); anxiety; pain; gastric stasis; symptoms of gastrointestinal dysfunction such as occur with dyspepsia, peptic ulcer, reflux oesophagitis and flatulence; migraine; and nausea and vomiting.

10 Claims, No Drawings

CARBAZOLE DERIVATIVES AND THEIR USE AS 5HT-INDUCED ANTAGONISTS

This invention relates to heterocyclic compounds, to processes for their preparation, to pharmaceutical compositions containing them and to their medical use. In particular the invention relates to compounds which act upon 5-hydroxytryptamine (5HT) receptors of the type located on terminals of primary afferent nerves.

According to one aspect the present invention provides a tetrahydrocarbazolone of the general formula (I):

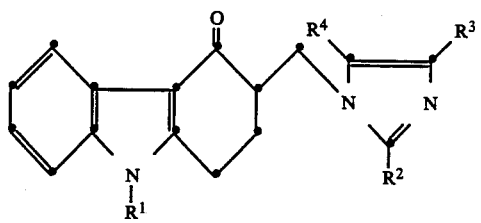

wherein
$P^1$ represents a group $CO_2R^5$, $COR^5$, $CONR^5R^6$ or $SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl-($C_{1-4}$)alkyl group, in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $CO_2R^5$ or $SO_2R^5$);
and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group; and physiologically acceptable salts and solvates thereof.

Referring to the general formula (I), the alkyl groups represented by $R^2$, $R^3$, $R^4$, $R^5$ and $R^6$ may be straight chain or branched chain alkyl groups, for example, methyl, ethyl, propyl, prop-2-yl, butyl, but-2-yl, 2-methylprop-2-yl, pentyl, pent-3-yl or hexyl.

An alkenyl group may be, for example, a propenyl group.

A phenyl-($C_{1-4}$)alkyl group may be, for example, a benzyl, phenethyl or 3-phenylpropyl group.

A cycloalkyl group may be, for example, a cyclopentyl, cyclohexyl or cycloheptyl group.

It will be appreciated that the carbon atom at the 3-position of the tetrahydrocarbazolone ring is asymmetric and may exist in the R- or S-configuration. Furthermore, it will be appreciated that depending upon the nature of the groups $R^2$, $R^3$, $R^4$, $R^5$ and $R^6$, centres of isomerism may occur elsewhere in the molecule. The present invention encompasses both the individual isomeric forms of the compounds of formula (I) and all mixtures, including racemic mixtures, thereof.

Suitable physiologically acceptable salts of the compounds of general formula (I) include acid addition salts formed with organic or inorganic acids for example, hydrochlorides, hydrobromides, sulphates, phosphates, citrates, fumarates and maleates. The solvates may, for example, be hydrates.

A preferred class of compounds represented by general formula (I) is that wherein one of the groups represented by $R^2$, $R^3$ and $R^4$ represents a $C_{1-3}$ alkyl, $C_{3-6}$ cycloalkyl or $C_{3-6}$ alkenyl group and each of the other two groups, which may be the same or different, represents a hydrogen atom or a $C_{1-3}$ alkyl group. When $R^2$ represents a hydrogen atom, $R^3$ and/or $R^4$ preferably represents a $C_{1-3}$ alkyl group. When $R^2$ represents a $C_{1-3}$ alkyl group $R^3$ and $R^4$ both preferably represent hydrogen atoms.

Another preferred class of compounds is that wherein $R^5$ and $R^6$ (which may be the same or different) represent a $C_{1-6}$ alkyl group, e.g. methyl; or a phenyl group, optionally substituted by a $C_{1-4}$ alkyl group e.g. methyl.

Particularly preferred compounds according to the invention include:
1,2,3,9-tetrahydro-3-[(2-methyl-1H-imidazol-1-yl)methyl]-9-(methyl sulphonyl)-4H-carbazol-4-one;
1,2,3,9-tetrahydro-9-(methoxycarbonyl)-3-[(2-methyl-1H-imidazol-1-yl)methyl]-4H-carbazol-4-one;
1,2,3,9-tetrahydro-9-(4-methylbenzenesulphonyl)-3-[(2-methyl-1H-imidazol-1-yl)methyl]-4H-carbazol-4-one;
9-acetyl-1,2,3,9-tetrahydro-3-[(2-methyl-1H-imidazol-1-yl)methyl]-4H-carbazol-4-one; and
1,2,3,4-tetrahydro-N,N-dimethyl-3-[(2-methyl-1H-imidazol-1-yl)methyl]-4-oxo-9H-carbazole-9-carboxamide;
and their physiologically acceptable salts and solvates.

Compounds of the invention are potent and selective antagonists of 5HT-induced responses of the rat isolated vagus nerve preparation and thus act as potent and selective antagonists of the 'neuronal' 5-HT receptor type located on primary afferent nerves. Receptors of this type are also believed to be present in the central nervous system. 5-HT occurs widely in the neuronal pathways in the central nervous system and disturbance of these 5-HT containing pathways is known to alter behavioural syndromes such as mood, psychomotor activity, appetite and memory.

It is believed that compounds which antagonise the effect of 5HT at 5HT receptors of the type located on the terminals of primary afferent nerves will be useful in the treatment of conditions such as psychotic disorders, (e.g. schizophrenia and mania); anxiety; pain; gastric stasis; symptoms of gastrointestinal dysfunction such as occur with dyspepsia, peptic ulcer, reflux desophagitis and flatulence; migraine; and nausea and vomiting.

Unlike existing drug treatments for these conditions the compounds of the invention, because of their high selectivity for 5-HT receptors of the type located on primary afferent nerve terminals, would not be expected to produce undesirable side effects. Thus, for example neuroleptic drugs exhibit extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; pain; gastric stasis, symptoms of gastrointestinal dysfunction such as dyspepsia, reflux oesophagitis, peptic ulcer or flatulence; migraine; or nausea or vomiting, which comprises administering an effective amount of a compound of formula (I) or a physiologically acceptable salt or solvate thereof.

Accordingly, the invention also provides a pharmaceutical composition which comprises at least one compound selected from 9-acyl-3-imidazolylmethyltetrahyrocarbazolone derivatives of the general formula (I), and their physiologically acceptable salts and solvates, e.g. hydrates, adapted for use in human or veterinary medicine, and formulated for administration by any convenient route.

Such compositions may be formulated in conventional manner using one or more physiologically acceptable carriers or excipients.

Thus the compounds of the invention may be formulated for oral, buccal, parenteral, topical or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maise starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbitol acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for administration to man (of approximately 70 kg body weight) is 0.05 to 20 mg, preferably 0.1 to 10 mg of the active ingredient per unit dose which could be administered, for example, 1 to 4 times per day. The dose will depend on the route of administration and the body weight of the patient. It will be appreciated that it may be necessary to make routine variations to the dosage depending on the age and weight of the patient as well as the severity of the condition to be treated.

For oral administration a unit dose will preferably contain from 0.5 to 10 mg of the active ingredient. A unit dose for parenteral administration will preferably contain 0.1 to 10 mg of the active ingredient.

Aerosol formulations are preferably arranged so that each metered dose or 'puff' delivered from a pressurised aerosol contains 0.1 mg to 2 mg, of a compound of the invention, and each dose administered via capsules and cartridges in an insufflator or an inhaler contains 0.2 to 20 mg of a compound of the invention. The overall daily dose by inhalation will be within the range 0.4 to 80 mg. Administration may be several times daily, for example from 2 to 8 times giving for example 1, 2 or 3 doses each time.

The compounds of the invention may, if desired, be administered in combination with one or more other therapeutic agents, such as cytostatic agents, e.g. cisplatin or cyclophosphamide.

According to another aspect of the invention, compounds of general formula (I) and physiologically acceptable salts or solvates or physiologically acceptable equivalents thereof may be prepared by the general methods outlined hereinafter.

According to a first general process (A), a compound of general formula (I) or a physiologically acceptable salt or solvate or a physiologically acceptable equivalent thereof may be prepared by reacting a compound of general formula (II):

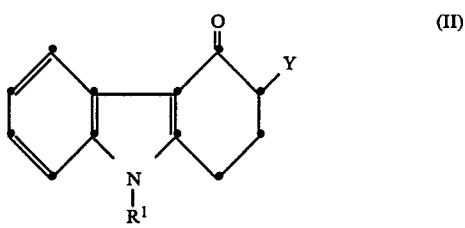

(II)

(wherein $R^1$ is as defined previously and Y represents a reactive substituent) or a protected derivative thereof with an imidazole of general formula (III):

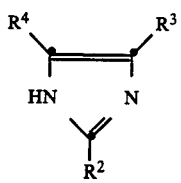

(III)

(wherein $R^2$, $R^3$ and $R^4$ are as defined previously) or a salt thereof.

Examples of compounds of formula (II) which may be employed as starting materials in the process (A) include compounds wherein Y represents a group selected from an alkenyl group $=CH_2$ or a group of formula $CH_2Z$ where Z represents a leaving atom or group such as a halogen atom, e.g. chlorine or bromine; an acyloxy group such as acetoxy, trifluoromethanesulphonyloxy, p-toluene sulphonyloxy or methanesulphonyloxy; a group $-N^+R^7R^8R^9E^-$, (where $R^7$, $R^8$ and $R^9$ each independently represents a lower alkyl e.g. methyl, aryl e.g. phenyl, or aralkyl e.g. benzyl and $E^-$ represents an anion such as a halide ion, e.g. chloride, bromide or iodide); or a group $-NR^7R^8$, where $R^7$ and $R^8$ are as previously defined, for example $-N(CH_3)_2$.

When Y represents the group $=CH_2$, the process may conveniently be carried out in a suitable solvent, examples of which include water; esters, e.g. ethyl acetate; ketones, e.g. acetone or methylisobutylketone; amides, e.g. dimethylformamide; alcohols, e.g. ethanol; and ethers e.g. dioxan or tetrahydrofuran; or mixtures thereof. The process may be effected at a temperature of, for example, 20° to 100° C.

When Y represents the group $CH_2Z$, where Z is a halogen atom or an acyloxy group, the process may conveniently be carried out in a suitable solvent such as an amide, e.g. dimethylformamide; an alcohol, e.g. methanol or industrial methylated spirit; or a haloalkane, e.g. dichloromethane, and at a temperature of from −10° to +150° C., e.g. +20° to +100° C.

The reaction of a compound of formula (II) where Y represents the group $CH_2Z$ where Z is the group $-N^+R^7R^8R^9E^-$, may conveniently be carried out in a suitable solvent such as water, an amide, e.g. dimethylformamide; a ketone, e.g. acetone; or an ether, e.g. dioxan, and at a temperature of from 20° to 150° C.

The reaction of a compound of formula (II) where Y represents the group $-CH_2Z$, where Z is the group $-NR^7R^8$, may conveniently be carried out in a suitable solvent such as water; an alcohol e.g. methanol; or an amide e.g. dimethylformamide, or mixtures thereof, and at a temperature of from 20° to 150° C.

The compounds of formula (II) are novel compounds and form a further feature of the invention.

The starting materials of formula (II) wherein Y represents the group $=CH_2$ may be prepared from compounds of formula (II) where Y represents the group $-CH_2N^+R^7R^8R^9E^-$ by reaction with a base in a suitable solvent. Examples of bases which may be employed include alkali metal hydroxides, e.g. potassium hydroxide, alkali metal carbonates or hydrogen carbonates e.g. sodium hydrogen carbonate, and tertiary amines, e.g. diisopropylethylamine.

The quaternary salts may be formed from the corresponding tertiary amine by reaction with an alkylating agent such as methyl iodide or dimethyl sulphate, if preferred in a suitable solvent, e.g. dimethylformamide. The tertiary amine (i.e. wherein Y represents a group $-CH_2NR^7R^8$) may be prepared by reaction of a tetrahydrocarbazolone of general formula (IV):

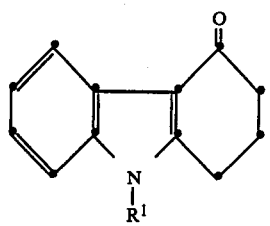

(IV)

(wherein $R^1$ is as defined previously) with formaldehyde and the corresponding secondary amine, if desired in a suitable solvent such as an alcohol, e.g. ethanol, or an organic acid e.g. acetic acid.

Compounds of general formula (IV) may be prepared for example, according to the method of processes (B), (C), (D) or (E) as described hereinafter using the appropriate starting materials.

The starting materials of general formula (II) where Y represents $-CH_2Y$ where Z is a halogen atom or an acyloxy group may be prepared from the corresponding hydroxymethyl derivative of general formula (V):

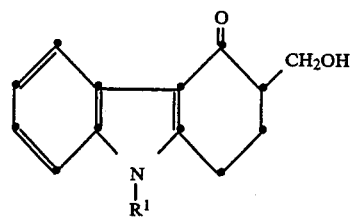

(V)

(wherein $R^1$ is as defined previously) which itself may be obtained by reacting the tetrahydrocarbazolone of general formula (IV) with formaldehyde, preferably in a suitable solvent such as an alcohol, e.g. ethanol, and preferably in the presence of a base.

Thus, the compounds where Z is a halogen atom may be obtained by reacting a compound of formula (V) with a halogenating agent such as a phosphorus trihalide, e.g. phosphorus trichloride.

The compounds where Z is an acyloxy group may be prepared by reacting a compound of formula (V) with an appropriate acylating agent such as an anhydride or a sulphonyl halide such as a sulphonyl chloride, optionally in the presence of a base e.g. triethylamine or pyridine.

Compounds of formula (II) where Y represents $-CH_2Z$ where Z is a halogen atom may also be prepared by reacting a compound for formula (11) where Y represents the group $=CH_2$ with the appropriate hydrogen halide, e.g. hydrogen chloride, conveniently, in a suitable solvent such as an ether, e.g. diethyl ether.

According to another general process (B) a compound of formula (I) may be prepared by oxidising a compound of formula (VI):

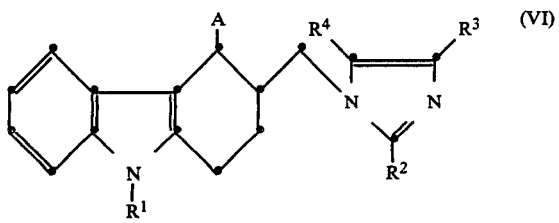

(wherein A represents a hydrogen atom or a hydroxyl group and $R^1$, $R^2$, $R^3$ and $R^4$ are as previously defined) or a salt or a protected derivative thereof.

The oxidation process may be effected using conventional methods. It will be appreciated that the reagents and reaction conditions should be chosen such that they do not cause oxidation of other parts of the molecule. Thus, the oxidation process is preferably effected using a mild oxidising agent.

When oxidising a compound of formula (VI) in which A represents a hydrogen atom, suitable oxidising agents include quinones in the presence of water, e.g. 2,3-dichloro-5,6-dicyano-1,4-benzoquinone or 2,3,5,6-tetrachloro-1,4-benzoquinone; selenium dioxide; a cerium (IV) oxidising reagent such as ceric ammonium nitrate or a chromium (VI) oxidising agent, e.g. a solution of chromic acid in acetone (for example Jones' reagent) or chromic trioxide in pyridine.

When oxidising a compound of formula (VI) in which A represents a hydroxyl group, suitable oxidising agents include quinones in the presence of water, e.g. 2,3-dichloro-5,6-dicyano-1,4-benzoquinone or 2,3,5,6-tetrachloro-1,4-benzoquinone; ketones, e.g. acetone, methylethylketone or cyclohexanone, in the presence of a base e.g. aluminium t-butoxide; a chromium (VI) oxidising agent, e.g. a solution of chromic acid in acetone (for example Jones reagent) or chromium trioxide in pyridine; an N-halosuccinimide, e.g. N-chlorosuccinimide or N-bromosuccinimide; a dialkylsuphoxide e.g. dimethylsulphoxide, in the presence of an activating agent such as N,N'-dicyclohexylcarbodiimide or an acyl halide, e.g. oxalyl chloride or tosyl chloride; pyridine-sulphur trioxide complex; or a dehydrogenation catalyst such as copper chromite, zinc oxide, copper or silver.

Suitable solvents may be selected from ketones, e.g. acetone or butanone; ethers e.g. tetrahydrofuran or dioxan; amides; e.g. dimethylformamide; hydrocarbons, e.g. benzene or toluene; halogenated hydrocarbons, e.g. dichloromethane; and water or mixtures thereof.

The process may be conveniently effected at a temperature of $-70°$ to $+50°$ C. It will be understood that the preferred reaction temperature will depend inter alia on the choice of oxidising agent.

Compounds of general formula (VI) may be prepared by reacting a compound of formula (VII):

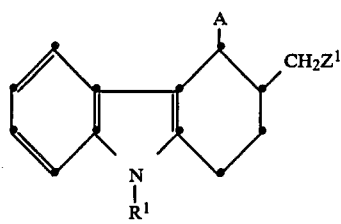

(wherein $R^1$ and A are as defined previously and $Z^1$ is a leaving atom or group such as a halogen atom, an acyloxy group or the group $-N^+R^7R^8R^9E^-$ as previously defined for Z) with an imidazole of formula (III) according to the method of process (A) described herein.

Compounds of general formula (VI) are novel compounds and form a further feature of this invention.

Compounds of formula (VII) may be prepared by reducing compounds of formula (II) using for example sodium borohydride.

Compounds of formula (VII) wherein A represents a hydrogen atom may also be prepared by reacting a compound of formula (VII) wherein A represents a hydroxyl group with a tosyl halide (e.g. tosyl chloride) and then reducing the resulting tosylate with for example sodium borohydride.

According to another general process (C), a compound of the formula (I) may be prepared by acylating a compound of formula (VIII):

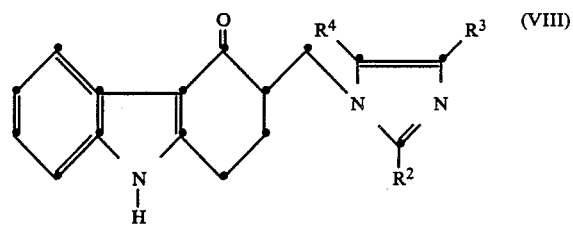

(wherein $R^2$, $R^3$ and $R^4$ are as defined previously) or a salt or protected derivative thereof with an acylating agent corresponding to the acid $R^1OH$.

Acylating agents corresponding to the acid $R^1OH$ include acid halides (e.g. an acid chloride, bromide or iodide), mixed and symmetrical anhydrides, lower alkylhaloformates (e.g. lower alkyl chloroformates), sulphonates (e.g. hydrocarbylsulphonates such as p-toluenesulphonate or methanesulphonate), carbonates and isocyanates, e.g. an isocyanate of formula $R^5NCO$.

The reaction may conveniently be effected in the presence of a base such as an alkali metal hydride e.g. sodium or potassium hydride, an alkali metal carbonate e.g. sodium or potassium carbonate, an alkali metal alkoxide e.g. potassium t-butoxide, butyllithium or an organic tertiary amine e.g. triethylamine or pyridine.

Suitable solvents which may be employed in general process (C) include amides (e.g. dimethylformamide or dimethylacetamide), ethers (e.g. tetrahydrofuran or dioxan), halogenated hydrocarbons (e.g. methylene chloride), nitriles (e.g. acetonitrile) and esters (e.g. ethyl acetate). The reaction may conveniently be effected at a temperature of from $-10°$ to $+150°$ C.

Compounds of formula (VIII) may be prepared for example by methods analogous to any processes (A), (B), (D) or (G) described herein, for example as described in UK Patent Application No. 2153821A.

According to another general process (D), a compound of formula (I) according to the invention or a salt or protected derivative thereof may be converted into another compound of formula (I) using conventional techniques. Such conventional techniques include hydrogenation, which may, for example, be used to convert an alkenyl substituent into an alkyl substituent.

Hydrogenation according to general process (D) may be effected using conventional procedures, for example by using hydrogen in the presence of a noble metal catalyst e.g. palladium, palladium oxide, Raney nickel, platinum, platinum oxide or rhodium. The catalyst may be supported on for example charcoal, or a homogeneous catalyst such tri(triphenylphosphine) rhodium chloride may be used. The hydrogenation will generally be effected in a solvent such as an alcohol, e.g. ethanol; an amide, e.g. dimethylformamide; an ether, e.g. dioxan; or an ester, e.g. ethyl acetate, and at a temperature in the range −20° to 100° C., preferably 0° to 50° C.

According to another general process (E), a compound of formula (I) may be prepared by cyclising a compound of formula (IX):

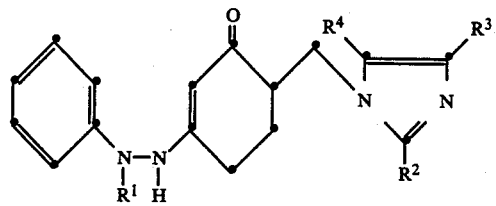

(wherein $R^1$, $R^2$, $R^3$ and $R^4$ are as defined previously) or a salt or a protected derivative thereof.

The cyclisation may be carried out in aqueous or non-aqueous media, in the presence of an acid catalyst. When an aqueous medium is employed this may be water or an aqueous organic solvent such as an aqueous alcohol (e.g. methanol, ethanol or isopropanol) or an aqueous ether (e.g. dioxan or tetrahydrofuran) as well as mixtures of such solvents. The acid catalyst may be, for example, an inorganic acid such as concentrated hydrochloric or sulphuric acid. (In some cases the acid catalyst may also act as the reaction solvent). In an anhydrous reaction medium, which may comprise one or more alcohols or ethers (e.g. as described above), carboxylic acids (e.g. acetic acid) or esters (e.g. ethyl acetate), the acid catalyst will generally be a Lewis acid such as boron trifluoride, zinc chloride or magnesium chloride.

Alternatively the cyclisation process may be carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

The cyclisation reaction may be conveniently carried out at temperatures of from 20° to 200° C., preferably 50° to 125° C.

According to a particular embodiment of general process (E), compounds of general formula (I) may be prepared directly by the reaction of a compound of formula (X):

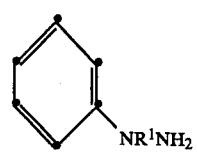

(wherein $R^1$ is as defined previously) or a salt thereof with a compound of formula (XI)

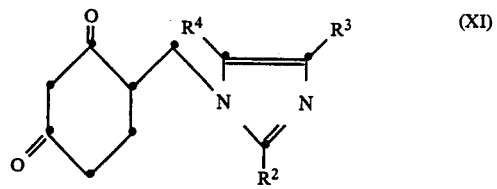

(wherein $R^2$, $R^3$ and $R^4$ are as defined previously) or a protected derivative thereof using the appropriate conditions as described above.

Compounds of general formula (IX) may be isolated as intermediates during the process for the preparation of compounds of general formula (I) wherein a compound of formula (X), or a salt thereof, is reacted with a compound of formula (XI) or a protected derivative thereof, in a suitable solvent such as an aqueous alcohol (e.g. methanol) and at a temperature of, for example, from 20° to 100° C.

A protected derivative of general formula (XI) may example have one or both of the carbonyl groups protected e.g. as an enol ether. It will be appreciated that when a compound of formula (XI) is used in which the carbonyl group at the 3-position is protected, it may be necessary to remove the protecting group in order for reaction to occur with the compound of formula (X). Deprotection may be carried out by conventional methods, as described hereinafter. If desired, deprotection may be effected in situ.

The compounds of formula (XI) may be prepared by reacting an imidazole of formula (III) with a compound of formula (XII):

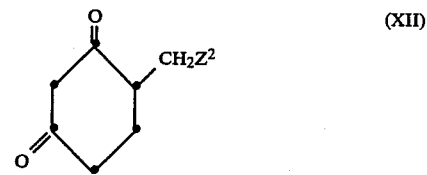

(wherein $Z^2$ is a readily displaceable atom or group such as a halogen atom, an acyloxy group or the group $-N^+R^7R^8R^9E^-$ as previously defined for Z) or a protected derivative thereof, according to the method of process (A) described herein.

The compounds of formula (XII) may be prepared by analogous methods to those described herein for the preparation of compounds of formula (II). For example, the compounds of formula (XII) wherein Z represents the group $N^+(CH_3)_3I^-$ may be prepared by a Mannich reaction using a cyclohexane-1,3-dione derivative in which one of the carbonyl groups is protected (for example as the methyl enol ether) followed by methylation. Thus the protected dione may be reacted with formaldehyde and dimethylamine, or more conveniently, the enolate may be reacted with Eschenmoser's salt $[CH_2=N^+(CH_3)_2I^-]$, followed by a methylating agent such as methyl iodide.

According to another general process (F) a compound of formula (I) may be prepared by cyclising a compound of formula (XIII):

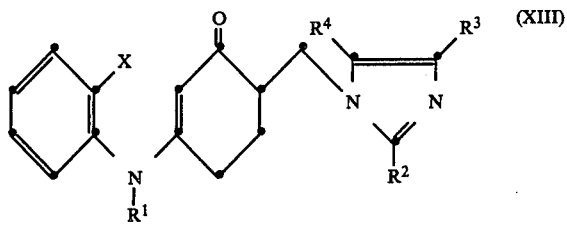

(wherein X represents a hydrogen atom or a halogen atom and $R^1$, $R^2$, $R^3$ and $R^4$ are as defined previously) or a salt or protected derivative thereof.

When X represents a halogen atom it may be, for example, a chlorine atom or, preferably, a bromine or iodine atom.

The reaction may be effected in the presence of a palladium reagent, or, when X represents a halogen atom, in the presence of a copper (I) salt or photochemically.

The palladium reagent may be, for example, a palladium salt derived from an organic acid, e.g. an acetate, or derived from an inorganic acid, e.g. a chloride or bromide, a palladium complex such as a triarylphosphine palladium complex, e.g. a triphenylphosphine or tri(2-methylphenyl)phosphine palladium complex, or finely divided palladium metal such as palladium on charcoal. The triarylphosphine palladium complex may be generated in situ by reacting a palladium salt, e.g. palladium acetate, with the appropriate triarylphosphine.

When a palladium reagent is used in the above process, the reaction may be effected in the presence or absence of a solvent. Suitable solvents include nitriles, e.g. acetontrile; alcohols e.g. methanol or ethanol; amides e.g. dimethylformamide, N-methylpyrrolidone or hexamethylphosphoramide; and water. The reaction may conveniently be carried out at a temperature of from 25° to 200° C. preferably 50° to 160° C.

When a compound of formula (XIII) in which X represents a halogen atom is used, the palladium reagent is preferably used in the presence of a base. Only a catalytic quantity of the reagent will then be required. Suitable bases include tertiary amines e.g. triethylamine or tri-n-butylamine; and alkali metal carbonates, bicarbonates or acetates, e.g. sodium or potassium carbonate, bicarbonate or acetate.

When a compound of formula (XIII) in which X represents a halogen atom other than an iodine atom, e.g. a chlorine or bromine atom is used, the palladium reagent, which may be generated in situ, is preferably a triarylphosphine palladium complex.

When a compound of formula (XIII) in which X represents a hydrogen atom is used, the palladium reagent is preferably a palladium salt. The reaction may conveniently be effected in the presence of an oxidising agent such as a copper (II) or silver salt e.g. cupric acetate or silver acetate in the presence of oxygen. Only a catalytic quantity of the palladium reagent will then be required.

A compound of general formula (XIII) wherein X represents a halogen atom may be cyclised according to general process (F) in the presence of a copper (I) salt, for example, copper (I) iodide. The reaction may be effected in the presence of a strong base, e.g. an alkali metal hydride such as sodium hydride or an alkali metal alkoxide such as sodium ethoxide. Suitable solvents include amides, e.g. dimethylformamide, N-methylpyr-rolidone or hexamethylphosphoramide; nitriles, e.g. acetonitrile; and alcohols, e.g. ethanol. The reaction may conveniently be effected at a temperature of 50° to 200° C., preferably 100° to 170° C.

When X represents a halogen atom cyclisation according to general process (F) may also be effected photochemically, conveniently by irradiating for example with a mercury lamp, preferably a high pressure mercury lamp. Suitable solvents for the reaction include nitriles, e.g. acetonitrile; chlorinated hydrocarbons e.g. carbon tetrachloride; and cyclic ethers, e.g. tetrahydrofuran or dioxan. The reaction may conveniently be effected in the presence of a base such as a tertiary amine, e.g. triethylamine.

The compounds of formula (XIII) may be prepared by reacting a compound of formula (XI) as previously defined or a salt thereof with a compound of formula (XIV).

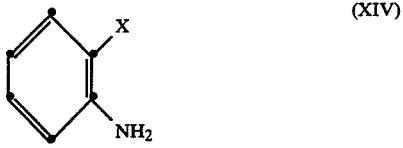

(wherein X is as defined previously), followed by acylation to introduce the group $R^1$, for example by methods analogous to process (A) described herein.

The reaction may conveniently be effected in an aqueous solvent such as water.

It should be appreciated that in some of the above transformations it may be necessary or desirable to protect any sensitive groups in the compound to avoid undesirable side reactions. The protecting groups used in the preparation of compounds of formula (I) are desirably groups which may be readily split off at a suitable stage in the reaction sequence, conveniently at the last stage. For example, during any of the reaction sequences described above, it may be necessary to protect the keto group. The carbonyl protecting group may be a conventional carbonyl protecting group such as those described in "Protective Groups in Organic Chemistry" Ed. J. F. W. McOmie (Plenum Press 1973) or "Protective Groups in Organic Synthesis" by Theodora W. Greene (John Wiley and Sons 1981). Thus for example, it may be a ketal such as a dialkyl or cyclic ketal, formed with an appropriate alkylorthoformate or diol, a thioketal, a bisulphite addition complex or an enol ether.

Compounds of general formula (I) may thus be prepared according to another general purpose (G), which comprises removal of any protecting groups from a protected form of a compound of formula (I). Deprotection may be effected using conventional techniques such as those described in 'Protective Groups in Organic Chemistry' Ed. J. F. W. McOmie (Plenum Press, 1973). Thus, a ketal such as an alkyleneketal group may be removed by treatment with a mineral acid such as hydrochloric acid. A thioketal group may be cleaved by treatment with a mercuric salt, e.g. mercuric chloride, in a suitable solvent, such as ethanol. An enol ether may be hydrolysed in the presence of an aqueous acid e.g. diulte sulphuric or hydrochloric acid.

The compounds of formula (I) may be converted into their physiologically acceptable salts according to conventional methods. Thus, for example, the free base of general formula (I) may be treated with an appropriate acid, preferably with an equivalent amount in a suitable solvent (e.g. aqueous ethanol).

Physiologically acceptable equivalents of a compound of formula (I) may be prepared according to conventional methods. Thus for example the free base of general formula (I) may be treated with an appropriate acid, preferably with an equivalent amount, in a suitable solvent.

Individual enantiomers of the compounds of the invention may be obtained by resolution of a mixture of enantiomers (e.g a racemic mixture) using conventional means, such as an optically active resolving acid; see for example 'Stereochemistry of Carbon Compounds' by E. L. Eliel (McGraw Hill 1962) and 'Tables of Resolving Agents' by S. H. Wilen.

Examples of optically active resolving acids that may be used to form salts with the racemic compounds include the (R) and (S) forms of organic carboxylic and sulphonic acids such as tartaric acid, di-p-toluoyltartaric acid, lactic acid and camphorsulphonic acid. The resulting mixture of isomeric salts may be separated, for example, by fractional crystallisation, into the diastereoisomers and if desired, the required optically active isomer may be converted into the free base.

The methods indicated above for preparing the compounds of the invention can be used as the last main step in the preparative sequence. The same general methods can be used for the introduction of the desired groups at an intermediate stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The following Preparations and Examples illustrate the invention. All temperatures are in °C.

Chromatography was carried out either in the conventional manner using silica gel (Merck, Kieselgel 60, Art. 7734 or 7747) or by flash chromatography (W. C. Still, M. Kahn and A. Mitra, *J. Org. Chem.* 1978, 43, 2933) on silica (Merck 9385) and thin layer chromatography (t.l.c.) on silica (Macherly-Nagel, Polygram) except where otherwise stated. The following abbreviations define the eluent used for chromatography and t.l.c.:

(A) Dichloromethane-ethanol-0.88 ammonia: 100:8:1,
(B) Dichloromethane-ethanol-0.88 ammonia: 200:10:1,
(C) Dichloromethane-methanol: 9:1,
(D) Dichloromethane-methanol: 15:1.

Intermediates were checked for purity by t.l.c. employing u.v. light for detection and spray reagents such as a solution of iodoplatinic acid (i.p.a.).

Proton ($^1$H) nuclear magnetic resonance (n.m.r.) spectra were obtained at 250 MHz using a Bruker AM or WM 250 instrument.

In the $^1$H n.m.r. data, the positions of the protons are numbered with reference to the following formula:

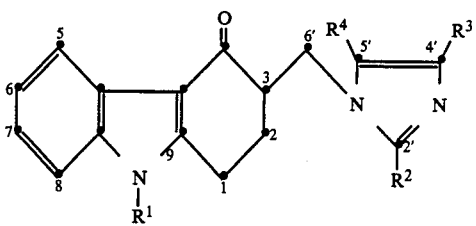

1,2,3,9-Tetrahydro-3-[(2-methyl-1H-imidazolyl-1-yl)methyl]-4H-carbazol-4-one, used as a starting material in the following Examples, is described in Example 3(b) of UK Patent Application No. 2153821A.

EXAMPLE 1

1,2,3,9-Tetrahydro-3-[(2-methyl-1H-imidazol-1-yl)methyl]-9-(methyl sulphonyl)-4H-carbazol-4-one maleate Sodium hydride (0.075 g) was added to a solution of 1,2,3,9-tetrahydro-3-[(2-methyl-1H-imidazol-1-yl)methyl]-4H-carbazol-4-one (0.7 g) in dimethylformamide (10 ml) and the mixture was stirred for 30 min. Methanesulphonyl chloride (0.25 ml) was added and stirring continued at room temperature for 5 h. The resulting solution was partitioned between sodium carbonate (100 ml) and ethyl acetate (3×50 ml). The combined organic layers were washed with water (3×50 ml), dried ($Na_2SO_4$), and evaporated in vacuo to give an oil. Purification by flash chromatography (A) gave an oil, which was dissolved in ethanol (10 ml) and added to a solution of maleic acid (0.15 g) in ethanol (5 ml). Addition of dry ether precipitated the title compound (0.7 g) m.p. 141°–142.5°.

T.l.c. (A), Rf 0.4.

Nmr δ(DMSO-$d_6$) includes 2.0–2.3 (m, $CH_2$-2); 2.67(s, $CH_3$-2'); 3.0–3.6(m, $CH_2$-1 and H-3); 4.07(s, —$CO_2CH_3$); 4.28 and 4.68(m, $CH_2$-6'); 7.3–7.5(m, aromatic H-6 and 7); 7.61 and 7.69(m, H-4' and 5'); and 8.05–8.15(m, aromatic H-5 and 8).

EXAMPLE 2

1,2,3,9-Tetrahydro-9-(methoxycarbonyl)-3-[(2-methyl-1H-imidazol-1-yl)methyl]-4H-carbazol-4-one maleate Sodium hydride (0.075 g) was added to a solution of 1,2,3,9-tetrahydro-3-[(2-methyl-1H-imidazol-1-yl)methyl]-4H-carbazol-4-one (0.7 g) in dimethylformamide (10 ml) and the mixture was stirred at room temperature for 30 min. Methyl chloroformate (0.3 ml) was added and stirring continued at room temperature for 4 h. The resulting solution was basified with sodium carbonate (100 ml) filtered, and the filtrate was extracted with ethyl acetate (2×50 ml). The combined organic extracts and solid were washed with water (3×50 ml), dried ($Na_2SO_4$) and evaporated in vacuo to give a solid. Purification by flash chromatography (A) gave a solid, which was dissolved in ethanol (5 ml) and added to a solution of maleic acid (0.018 g) in ethanol (5 ml) to give the title compound (0.07 g) m.p. 91°–92°.

T.l.c. (A), Rf 0.35.

Analysis Found: C, 56.8; H, 4.7; N, 7.7. $C_{19}H_{19}N_3O_3.1.5C_4H_4O_4.H_2O$ requires C, 56.7; H, 4.7; N, 7.9%.

Nmr δ(DMSO-$d_6$) includes 2.0–2.3(m, $CH_2$-2); 2.63(s, $CH_2$-2'); 3.1–3.6(m, $CH_2$-1 and H-3); 3.68(s, —$SO_2CH_3$); 4.31 and 4.67(m, $CH_2$-6'); and 7.4–7.5 and 8.1–8.2(m, aromatic protons).

EXAMPLE 3

1,2,3,9-Tetrahydro-9-(4-methylbenzenesulphonyl)-3-[(2-methyl-1H-imidazol-1-yl)methyl]-4H-carbazol-4-one maleate A stirred solution of 1,2,3,9-tetrahydro-3-[(2-methyl-1H-imidazol-1-yl)methyl]-4H-carbazol-4-one (0.55 g) in dry dimethylformamide (15 ml) was treated with sodium hydride (0.06 g). After 1 h p-toluenesulphonyl chloride (0.45 g) was added. After a further 4 h the mixture was partitioned between sodium carbonate (2N, 300 ml) and ethyl acetate (3×100 ml). The organic phase was washed with water (6×100 ml), dried (Na$_2$SO$_4$), evaporated to dryness and the resulting foam purified by flash chromatography (B) to give a foam (0.5 g). This was dissolved in hot ethyl acetate (100 ml) and treated with a solution of maleic acid (0.15 g) in ethyl acetate (20 ml). The title compound crystallised on cooling (0.6 g) m.p. 174°–175°.

Nmr δ(DMSO-d$_6$) includes 2.0–2.3, 3.2–3.4 and 3.2–3.7 (m, aliphatic tetrahydrocarbazolone protons); 2.64(s, CH$_3$-2') 2.37 (—SO$_2$—(C$_6$H$_4$)—CH$_3$); 4.27 and 4.67 (m, CH$_2$-6'); 7.3–7.5 and 8.1–8.2 (m, aromatic tetrahydrocarbazolone protons); and 7.46 and 7.97(SO$_2$—(C$_6$H$_4$)—CH$_3$).

EXAMPLE 4

9-Acetyl-1,2,3,9-tetrahydro-3-[(2-methyl-1H-imidazol-1-yl)methyl]-4H-carbazol-4-one A mixture of 1,2,3,9-tetrahydro-3-[(2-methyl-1H-imidazol-1-yl)methyl]-4H-carbazol-4-one (0.5 g) and 80% sodium hydride dispersion in mineral oil (0.07 g) in dry dimethylformamide (10 ml) was stirred under nitrogen until hydrogen evolution had ceased (ca. 0.5 h). The mixture was cooled to 0° and acetyl chloride (0.18 g) was added. The mixture was stirred at 0° for 1 h, diluted with 8% aqueous sodium bicarbonate (50 ml) and extracted with dichloromethane (2×50 ml). The dried (Na$_2$SO$_4$) extracts were evaporated to give a solid which was purified by flash chromatography (C) to give a solid (0.25 g). Recrystallisation from ethyl acetate-methanol afforded the title compound as crystals (0.12 g) m.p. 173°–175°.

Nmr δ(CDCl$_3$) includes 1.8–2.3, 2.88 and 3.1–3.5 (aliphatic tetrahydrocarbazolone protons); 2.43(s, CH$_3$-2'); 2.82(s, COCH$_3$); 4.08 and 4.62(m, CH$_2$-6'); and 7.35–7.45, 7.83 and 8.33(m, aromatic tetrahydrocarbazolone protons).

EXAMPLE 5

1,2,3,4-Tetrahydro-N,N-dimethyl-3-[(2-methyl-1H-imidazol-1-yl)methyl]-4-oxo-9H-carbazole-9-carboxamide hydrochloride A mixture of 1,2,3,9-tetrahydro-3-[(2-methyl-1H-imidazol-1-yl)methyl]-4H-carbazol-4-one (0.5 g) and 80% sodium hydride dispersion in mineral oil (0.06 g) in dry dimethylformamide (10 ml) was stirred at 23° under nitrogen until hydrogen evolution had ceased (ca 0.5 h). Dimethylcarbamoyl chloride (0.25 g) was added and stirring was continued at 23° for 4 h. The mixture was diluted with 8% aqueous sodium bicarbonate (50 ml), extracted with dichloromethane (3×30 ml) and the dried (Na$_2$SO$_4$) organic extracts were evaporated to give an oil. Purification by flash chromatography (ether and D) afforded the free base (0.41 g) as an oil. This was dissolved in dichloromethane (15 ml) and treated with excess ethereal hydrogen chloride. The mixture was evaporated and the residual gum triturated with dry ether to give the title compound as a solid (0.42 g) m.p. 200°–202° (decomp.).

N.m.r. δ(DMSO-d$_6$) includes 2.0–2.2 and 3.0–3.5 (m, aliphatic tetrahydrocarbazolone protons); 2.69(s, CH$_3$-2'); 3.08(s, CONH(CH$_3$)$_2$); 4.30 and 4.70 (m, CH$_2$-6'); and 7.3–7.4, 7.47 and 8.08 (m, aromatic tetrahydrocarbazolone protons).

The following examples illustrate pharmaceutical formulations according to the invention.

TABLETS FOR ORAL ADMINISTRATION

Tablets may be prepared by the normal methods such as direct compression of wet granulation.

The tablets may be film coated with suitable film forming materials, such as hydroxypropyl methylcellulose, using standard techniques. Alternatively the tablets may be sugar coated.

Direct Compression

| Tablet | mg/tablet |
| --- | --- |
| Active Ingredient | 8.0 |
| Lactose NF* | 89.5 |
| Croscarmellose Sodium NF | 2.0 |
| Magnesium Stearate BP | 0.5 |
| Compression weight | 100.0 |

*of a grade suitable for direct compression.

The active ingredient is passed through a 60 mesh sieve, blended with the lactose, croscarmellose sodium and magnesium stearate. The resultant mix is compressed into tablets using 5.5 mm diameter punches.

Tablets of other strengths may be prepared by altering the ratio of active ingredient to lactose or the compression weight and using punches to suit.

FORMULATION FOR INJECTION

|  | mg/ml |
| --- | --- |
| Active Ingredient | 2.0 |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A compound of formula (I):

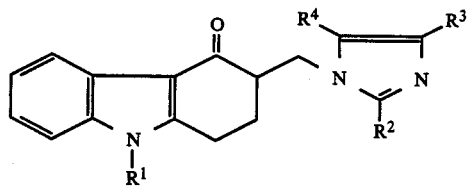

wherein
R¹ represents a group $CO_2R^5$, $COR^5$, $CONR^5R^6$ or $SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl-($C_{1-4}$)alkyl group in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $CO_2R^5$ or $SO_2R^5$);

and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group; or physiologically acceptable salt or solvate thereof.

2. A compound as claimed in claim 1, in which one of the groups represented by $R^2$, $R^3$ and $R^4$ represents a $C_{1-3}$ alkyl, $C_{3-6}$ cycloalkyl or $C_{3-6}$ alkenyl group and each of the other two groups, which may be the same or different, represents a hydrogen atom or a $C_{1-3}$ alkyl group.

3. A compound as claimed in claim 1 in which $R^2$ represents a hydrogen atom and one of the groups $R^3$ and $R^4$ represents a $C_{1-3}$ alkyl group.

4. A compound as claimed in claim 1 in which $R^2$ represents a hydrogen atom and $R^3$ and $R^4$ both represent a $C_{1-3}$ alkyl group.

5. A compound as claimed in claim 1 in which $R^2$ represents a $C_{1-3}$ alkyl group and $R_3$ and $R_3$ both represent a hydrogen atom.

6. A compound as claimed in claim 1 in which $R^5$ and $R^6$ (which may be the same or different) represent a $C_{1-6}$ alkyl group; or a phenyl group optionally substituted by a $C_{1-4}$ alkyl group.

7. A compound selected from the group consisting of
1,2,3,9-tetrahydro-3-[(2-methyl-1H-imidazol-1-yl)methyl]-9-(methylsulphonyl)-4H-carbazol-4-one;
1,2,3,9-tetrahydro-9-(methoxycarbonyl)-3-[(2-methyl-1H-imidazol-1-yl)methyl]-4e,uns/H/-carbazol-4-one;
1,2,3,9-tetrahydro-9-(4-methylbenzenesulphonyl)-3-[(2-methyl-1H-imidazol-1-yl)methyl]-4H-carbazol-4-one;
9-acetyl-1,2,3,9-tetrahydro-3-[(2-methyl-1H-imidazol-1-yl)methyl]-4H-carbazol-4-one;
1,2,3,4-tetrahydro-N,N-dimethyl-3-[(2-methyl-1H-imidazol-1-yl)methyl]-4-oxo-9H-carbazole-9-carboxamide;
a physiologically acceptable salt or a solvate thereof.

8. A pharmaceutical composition for the treatment of a condition caused by disturbance of "neuronal" 5HT function comprising at least one compound of formula (I) as defined in claim 1 or a physiologically acceptable salt or solvate thereof in an amount effective to relieve said condition together with at least one physiologically acceptable carrier or excipient.

9. A method of treating a condition caused by disturbance of "neuronal" 5HT function with comprises administering to a patient an effective amount of a compound of formula (I) as defined in claim 1 or a physiologically acceptable salt or solvate thereof to relieve said condition.

10. A compound of formula (VI)

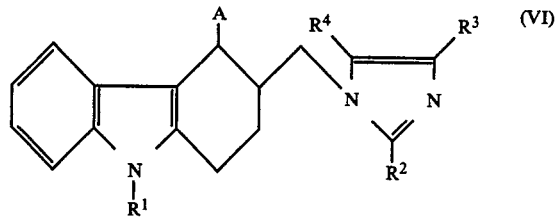

wherein
R¹ represents a group $CO_2R^5$, $COR^5$, $CONR^5R^6$ or $SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl-($C_{1-4}$)alkyl group in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $CO_2R^5$ or $SO_2R^5$);

and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group; and A represents a hydrogen atom or a hydroxyl group.

* * * * *

UNITED STATES PATENT AND TRADEMARK OFFICE
CERTIFICATE OF CORRECTION

PATENT NO. : 4,749,718
DATED : June 7, 1988
INVENTOR(S) : Ian H. Coates et al

It is certified that error appears in the above-identified patent and that said Letters Patent is hereby corrected as shown below:

Please correct the title to read:   --CARBAZOLE DERIVATIVES AND THEIR USE AS 5HT ANTAGONISTS--.

Column 17, line 29, before 'physiologically' please insert --a--.

Column 18, line 2, please delete "1H-imidazol-1-yl)methyl]-4e,uns/H/-carbazol-" and insert --1H-imidazol-1-yl)methyl]-4H-carbazol- --.

Signed and Sealed this

Eighteenth Day of April, 1989

Attest:

DONALD J. QUIGG

*Attesting Officer*          Commissioner of Patents and Trademarks